United States Patent [19]

Fraatz et al.

[11] Patent Number: 5,372,936
[45] Date of Patent: Dec. 13, 1994

[54] METHOD FOR DETECTING BIOLOGICAL ACTIVITIES IN A SPECIMEN

[75] Inventors: Robert Fraatz, Woodstock; Ewald Joebstl, Roswell, both of Ga.; Hellfried Karpf, Graz, Austria

[73] Assignee: AVL Photoronics Corporation, Roswell, Ga.

[21] Appl. No.: 108,540

[22] Filed: Aug. 19, 1993

Related U.S. Application Data

[60] Division of Ser. No. 501,123, Mar. 29, 1990, Pat. No. 5,266,486, which is a continuation-in-part of Ser. No. 474,786, Mar. 29, 1990, Pat. No. 5,217,875.

[30] Foreign Application Priority Data

May 12, 1989 [AT] Austria .............................. A1147/89

[51] Int. Cl.$^5$ ..................... C12Q 1/04; C12M 1/34; G01N 21/76
[52] U.S. Cl. ................................. 435/34; 435/4; 435/29; 435/291; 435/294; 435/817; 435/968; 436/172; 436/800; 436/805; 382/6
[58] Field of Search ........................ 435/34, 4, 29, 291, 435/294, 817, 968; 436/172, 800, 805; 382/6

[56] References Cited

U.S. PATENT DOCUMENTS

| | | | |
|---|---|---|---|
| Re. 31,879 | 5/1985 | Lübbers et al. | 436/133 |
| 4,495,293 | 1/1985 | Shaffer | 436/172 |
| 4,608,344 | 8/1986 | Carter et al. | 436/34 |
| 4,810,655 | 3/1989 | Khalil et al. | 436/138 |
| 4,945,060 | 7/1990 | Turner et al. | 435/291 |
| 5,043,286 | 8/1991 | Khalil et al. | 436/136 |
| 5,217,875 | 6/1993 | Karpf et al. | 435/34 |

FOREIGN PATENT DOCUMENTS

| | | | |
|---|---|---|---|
| 0333253 | 3/1989 | European Pat. Off. | C12M 1/34 |
| WO82/04264 | 12/1982 | WIPO | C12Q 1/00 |

OTHER PUBLICATIONS

Japanese Patent 57207861, Patent Abstracts of Japan, vol. 7 No. 64 (P-183) (1209) Mar. 17, 1983.

"Biochemical Tests for Identification of Medical Bacteria", MacFaddin, The Williams & Wilkins Company, 1976 pp. 108–118 and pp. 187–194.

*Primary Examiner*—Jeffrey E. Russel
*Assistant Examiner*—Abdel A. Mohamed
*Attorney, Agent, or Firm*—Hill, Steadman & Simpson

[57] ABSTRACT

A method, a sensor and apparatus for detecting biological activities in a specimen, for example in a blood sample, are provided in which a sealable container is sealed with a culture medium therein into which the sample is introduced, metabolic processes are enhanced in the presence of microorganisms in the sample and changes taking place in the concentrations of the substances. Such processes are detected and monitored with an excitation and detection assembly assigned to concentration sensors, in the form of optodes which are optically coupled to the excitation and detection assembly and to thereby to an evaluation unit for determining concentration changes of the substances over time as indications of the presence of microorganisms.

6 Claims, 9 Drawing Sheets

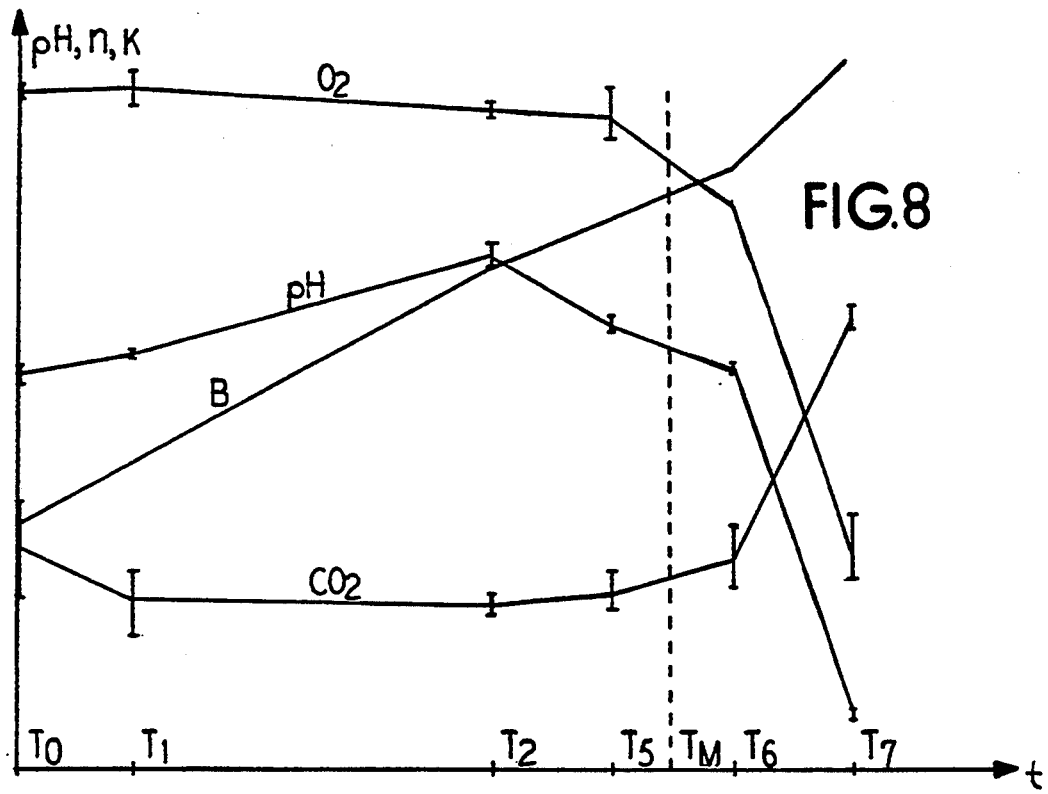
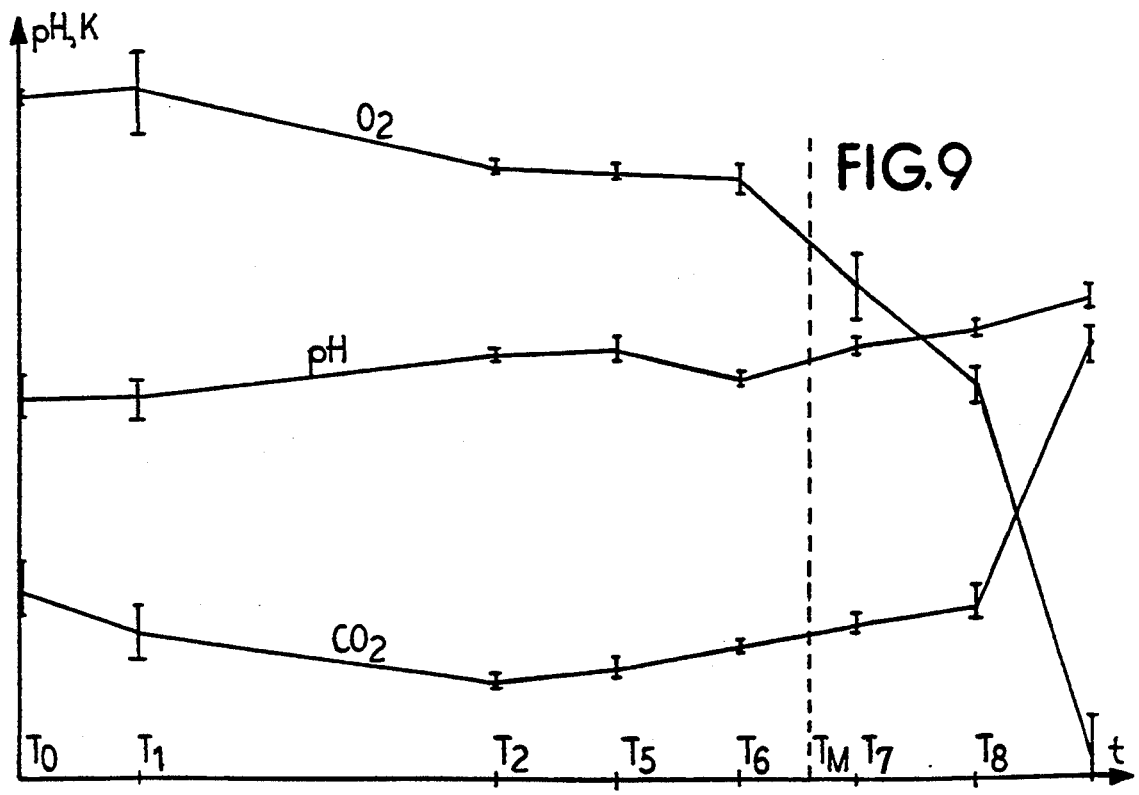

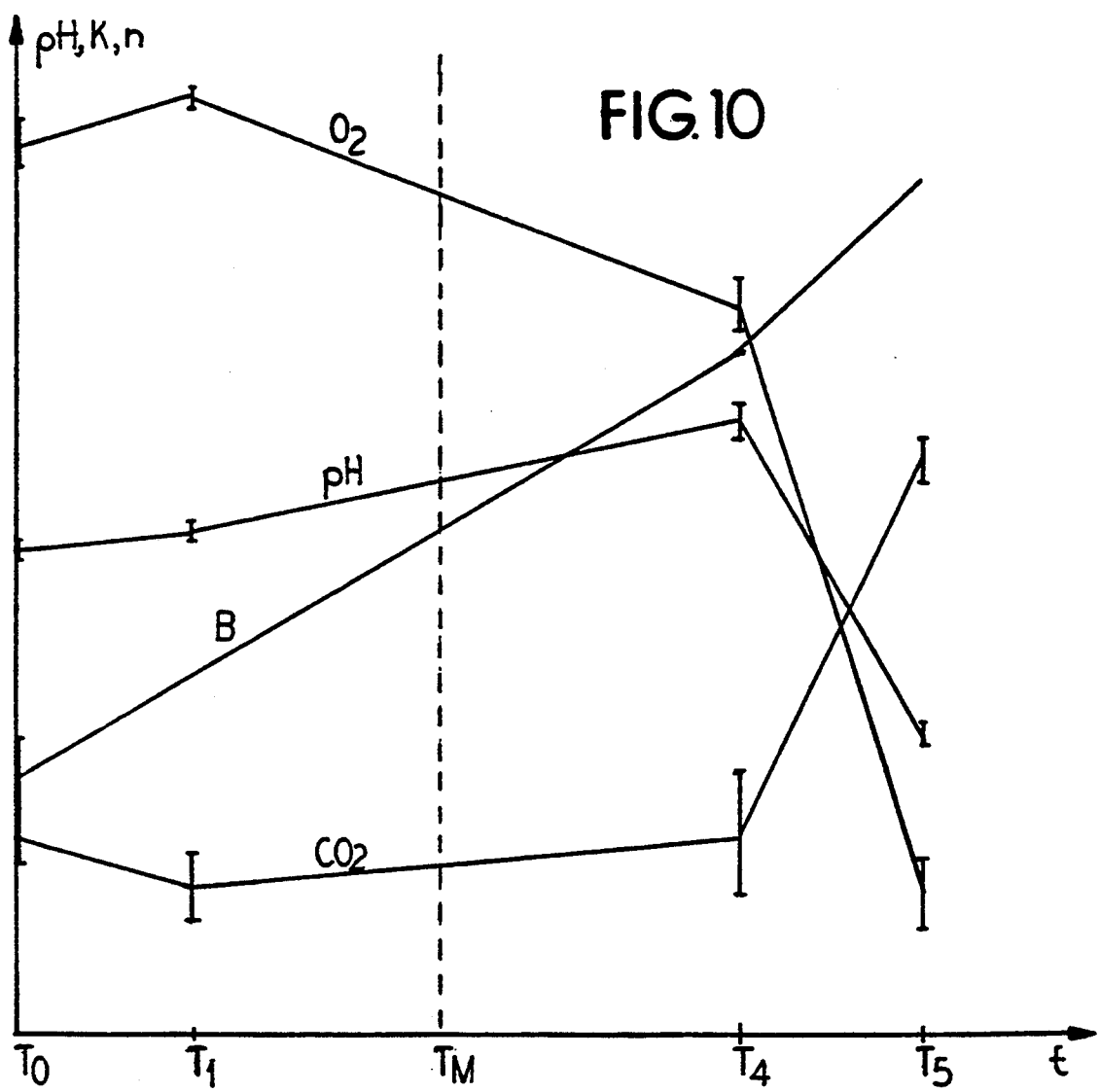

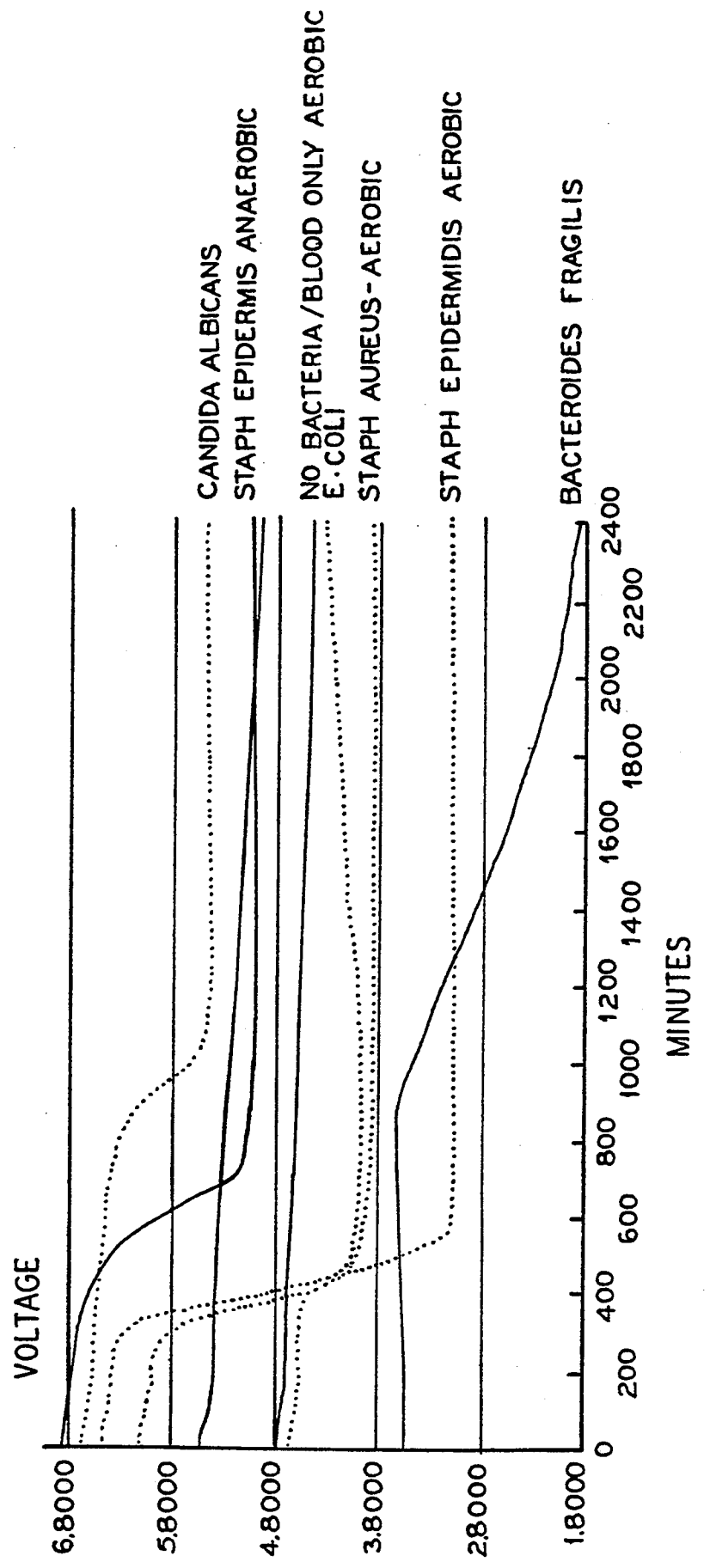

METHOD FOR DETECTING BIOLOGICAL ACTIVITIES IN A SPECIMEN

This is a division of application Ser. No. 07/501,123 filed Mar. 29, 1990, issued as U.S. Pat. No. 5,266,486, which is in turn a continuation-in-part of Ser. No. 474,786 filed Mar. 29, 1990, issued as U.S. Pat. No. 5,217,875.

BACKGROUND OF THE INVENTION

1. Field of the Invention

The present invention relates to a method and to an apparatus for detecting biological activities in a specimen where the specimen and a culture medium are introduced into a sealable container and are exposed to conditions enabling metabolic processes to take place in the presence of microorganisms in the sample, the concentration of the initial substances being lowered and that of metabolic products being raised.

2. Description of the Prior Art

In many applications it is necessary to determine quickly whether a specimen is contaminated by microorganisms, such as bacteria, in particular in medical applications, in the pharmaceutical industry, food industry, or in environmental protection activities. The term "specimen" has a most comprehensive meaning here, including substances such as solid and liquid biological material (e.g. blood), food samples, such as frozen foods and preserves or canned foods, packaging material, clinical instruments and laboratory equipment, or samples taken from their surfaces, medical apparatus, first-aid and dressing material, soil and water samples, particularly samples of drinking water.

For a long time purely manual methods have been used in which the specimen to be assessed is placed in a culture bottle containing a liquid culture medium, and the growth of the culture is inspected only visually at given time intervals, and the type of presence of a microorganism is inferred from this observation by subculturing the liquid culture medium to a solid culture medium.

In addition, some technical procedures and devices are known, with which the biological activities in a sample are caused by microorganisms may be determined, and where the $CO_2$ produced by the metabolism of the microorganism, or rather, the change in $CO_2$ content, is employed as a measurement for determining the biological activity.

It is a known procedure, for example, to bottle the sample to be assessed together with a radioactively-labeled liquid culture medium and to test the atmosphere over the culture medium for radioactive gases, following which the presence of microorganisms in the sample may be determined.

Measuring systems of this type are described in U.S. Pat. Nos. 3,076,679 and 3,935,073, for example, fully incorporated herein by this reference. Although such systems are quick and reliable, they have certain disadvantages, i.e. radioactive substances must be handled and samples must be repeatedly taken from the gas space above the culture medium for frequent monitoring. When the samples are removed from the gas space, the remaining samples to be monitored may easily be contaminated by the sample-taking element and measuring errors may occur.

In the European application 0 158 497, a system is disclosed in which the biological activity of the specimen is determined by means of infrared absorption. In this method, a specimen is introduced into a sealable vessel containing a liquid culture medium, and is tested for the presence of microorganisms. The vessel is subjected to specific conditions, i.e. certain temperatures are maintained over given periods of time, thus enhancing the metabolism of the microorganisms, during which process $CO_2$ is produced in the gas space above the culture medium by conversion of the carbon source. A sample is taken from the gas space and introduced into a measuring cell, and the $CO_2$ content is measured by infrared absorption. Again, the subsequent samples may be contaminated, and another drawback is that infrared absorption is a less-sensitive means of measuring than radioactive labeling.

In order to avoid the problem of cross-contamination, the European application 0 104 463 proposes a method and a device which are also based on teh detection of $CO_2$ (produced by metabolic processes) by means of infrared absorption. In this method, no sample is taken, but infrared radiation is directly transmitted through the wall of the vessel into the gas space above the culture medium, and its absorption is determined. Due to this non-invasive measuring method, cross-contaminations are largely eliminated; the disadvantage of this method, however, is its lack of sensitivity compared to radiometric methods; as well as the fact that the measurement is distorted by other gas components absorbing radiation in the same frequency band as $CO_2$. A suitable example is the absorption bands of water vapor. The sample vessels employed must be transparent within a relatively narrow frequency range, which will only permit the use of specific materials for these vessels. An additional disadvantage is that the generation and filtering of the required infrared radiation is comparatively complex and expensive.

The European application 0 333 253 describes a device and apparatus for monitoring changes in pH and $CO_2$ in a bacterial culture utilizing optical absorption measurements of a pH indicator in a matrix. Although it is not as sensitive as the radiometric method, it does offer the advantage of being noninvasive and can be continuously monitored. The primary disadvantage is that since color changes are being measured, different optical systems must then be used when the indicator medium is changed, thereby limiting the apparatus to one or two sensors.

SUMMARY OF THE INVENTION

It is therefore an object of the present invention to provide a method and an apparatus for detecting biological activities in a specimen, which have at least the same sensitivity as radiometric methods, and which offer the user a versatile, simple and inexpensive technique, providing him with information on the presence of microorganisms, while eliminating the danger of cross-contamination.

According to the present invention, the above object is achieved by continuously measuring the concentration of at least one (produced or consumed) substance subject to conversion by metabolic processes, generating a test signal by way of optodes in direct contact with the substances to be assessed, and monitoring the changes over time of the test signal or signals to serve as an indicator for the presence of microorganisms. The optical sensors or optodes which rely on the principle of fluorescence attenuation or enhancement, which may be inexpensively mass produced and which are in direct contact with the substance to be assessed and attached to a transparent surface of the container (internal filtered effect), permit continuous monitoring in closed systems, where new optodes are used for each sample, such that cross-contaminations are eliminated in the most simple variation, for example, a single sensor may suffice to determine the presence of microorganisms by way of the changes in substance concentrations relative to the initial concentrations.

With respect to the aforementioned disadvantage of measuring color changes and the requirement for different optical systems when an indicator medium is changed, another object of the present invention is to provide a sensor which allows the monitoring of many optical changes while utilizing the same optical system.

According to the present invention, the immediately-foregoing object is achieved by utilizing a inert fluorophore in the optode and measuring the modulation of the fluorescent output caused by optical changes in the indicator medium. It also provides for very sensitive continuously monitoring a noninvasive system.

The present invention provides that concentrations be measured of at least one substance from the group of $CO_2$, $O_2$, $H_+$ (pH), $NH_4^+$, $H_2S$, $H_2$, and metal ions, the indicator medium of the optodes responding to a change in substance concentrations by changing its optical characteristics such that a change in fluorescence intensity from an inert fluorescing component of the sensor is measured.

In particular, the invention provides, for example, for the testing of blood samples, that the $CO_2$ concentration be measured continuously and the detection of microorganisms be determined upon a rise of the $CO_2$ concentration. The invention further provides for using any combination of sensors to identify the microorganisms completely or partially.

In accordance with another variation, the invention will also permit continuous measuring of the $O_2$ concentration and determination of the changes in $H_2S$, $NH_4$ and pH. The advantage of this variation is that the significant changes in the $O_2$, $NH_4$, $H_2S$, and pH concentration may be detected earlier than the detection of changes of $CO_2$ alone.

The invention also provides that a culture medium containing a carbon compound be introduced into a sealable container, and that the sensor be added to the culture medium, which responds to the changes in metabolic substances content by a change in its fluorescence behavior, and that a blood sample be introduced into the container, which may be subject to metabolic processes in the presence of microorganisms, during which metabolic processes occur, and that the content of the container be exposed to excitation radiation and the radiation emitted by the fluorescent component of the sensor be measured, a change in fluorescence behavior indicating the presence of microorganisms. For example, indicator capsules as disclosed in the German application 23 63 84 may be added, or rather, microcapsules containing sensors, whose walls are made from polymerized hydrophilic monomers.

According to the invention, a device is provided for detecting biological activities in a specimen, comprising a sealable container containing a culture medium into which the sample is introduced, and further comprising means enabling metabolic processes to take place in the presence of microorganisms in the sample, and is characterized by the use of several optodes for simultaneous assessment of several substances whose concentrations are subject to changes by the metabolic processes, and by assigning an excitation and detection assembly to each optode, which, in turn, is connected with an evaluation unit for determining the change over time of the substance concentrations. Combining two optodes (e.g. $O_2$ and pH) to form a bisensor, or three optodes (e.g. $CO_2$, $O_2$, pH) to form a trisensor may be of advantage.

At this point, a description shall be provided with respect to the concepts, types of structure on a system and component basis, technology, principles of the invention and model systems for particular materials, all included in what is referred to as Fluorescence Intensity Modulation Sensor Technology (FIMST).

The present invention is based on certain fundamental concepts including the desire to use an inert fluorescent material in combination with an aqueous emulsion of an indicator to provide significant benefits due to:

1. Selection of a high quantum efficiency fluorophore;
2. Selection of fluorophore that has an absorptions match to an inexpensive and powerful excitation source;
3. Selection of an indicator that is most sensitive to the region of interest;
4. Selection of an indicator with a strong absorptions at either, or both, the excitation or emission wavelength of the fluorophore; and
5. The potential to use the same optical system (source and detector) for sensors detecting different analytes.

The structure of embodiments of the invention may utilize various components and variations including:

1. Membrane (e.g. gas permeable silicone)
    a. single membrane containing both the fluorescent material and the indicator, or
    b. a multi-layer structure with the fluorophore and indicator in separate layers;
2. Fluorescent material, fluorophore
    a. contained in the silicone, or
    b. contained in an aqueous emulsion;
3. Indicator
    a. contained in the aqueous emulsion,
    b. contained in the sample solution, or
    c. contained in the sensor matrix;
4. Source
    a. light emitting diodes (LEDs) including
        1. blue 456 nm peak or 470 nm peak,
        2. green 560 nm peak, 550—580 nm half intensity,
        3. yellow 590 nm peak, 570—610 nm half intensity,
        4. high intensity red (red/orange) 645 nm peak, 615—660 nm half intensity and
        5. red 665 nm peak, 650—670 nm half intensity; and
    b. other lamps such as tungsten, quartz halogen and neon; and
5. Detector
    a. silicon photodiodes,
    b. PIN silicon diodes,
    c. GaAsP photodiodes, and
    d. other photodetectors including photovoltaics, photoresistive devices and photoconductive devices.

The method disclosed herein has general applicability for the determination of any substance for which a colorimetric method and a permeable membrane can be prepared. Various principles may be used in selecting a sensor system and model sensor systems are discussed hereinbelow.

According to the principles of the invention, current optical sensors using fluorescence or absorbance-based materials have inherent limitations. The absorbance and fluorescence-based systems must use different optical systems (light source, filters and detectors) for each sensor system, depending on the optical change of the indicator medium. This is due to the necessity of providing and measuring different wavelengths of light for each different optical system.

The disadvantage for direct fluorescence detection of the metabolic substances of microorganisms is that the source and detectors for use in fluorescence are expensive and of limited availability. In addition, direct fluorescence systems have not yet been described for some tests of interest (e.g., hydrogen sulfide and ammonia).

A system constructed in accordance with the present invention has a sensor and an optical system that provides for the determination of a fluorescent intensity from the sensor. The optical unit has a light source that provides light of the appropriate wavelengths to excite the fluorescent material in the sensor. The light source may be filtered to provide light only at the wavelengths appropriate to the fluorophore. In the most simple case, the source is a light-emitting diode that provides transmission only at the wavelengths needed for excitation.

The detector can be any device that will provide an electronic signal proportional to the light intensity. The preferred embodiment uses a silicon photodiode with a filter to select only the fluorescent wavelength. In a preferred variation, the source and detector are held in a mount that positions the light from the lamp to illuminate the sensor directly above the photodetector. Appropriate optical filters are used to optimize the signal change associated with the optical change in the indicator medium.

The sensor is composed of two parts, an inert fluorescent material which provides the fundamental optical signal and, the indicator material. In practical applications, the sensor is placed and attached to a transparent surface inside a sealable container that can be filled with liquid media that supports the growth of microorganisms.

The fluorescent material is selected to provide an optical signal matched with the source and detector. The quantum efficiency of the fluorescent material will, to an extent, determine the detection range of the sensor system. The fluorescent material may be mixed in the sensor with the indicator material, incorporated as a part of the sensor matrix, applied as a coating to the back of the sensor or in any manner in which the light from the source will pass through the indicator before or after passing through the fluorescent material. The indicator material is selected to provide an optical change in response to the analyte at the concentrations expected. The sensitivity of the sensor system is determined by the amount which the color changes of the indicator interacts with (modulates) the excitation and/or emission of the fluorescent signal. In use, the sensor system provides a constant signal when the concentration of the analyte remains constant. When the analyte concentration changes, the indicator responds by exhibiting a change in optical properties (e.g., color intensity). This change acts as an optical filter to change the amount of light exciting or emitted from the fluorescent substrate. This change in light is detected as an amplitude change (modulation) by the appropriately-filtered photodetector.

A number of different configurations are possible in this sensor system including having separate layers of silicon membrane for the fluorescent material and the indicator. In a preferred variation, the optode is covered with a dye-impregnated silicone to maintain optical isolation for the system. Examples of the construction of the sensor are presented in Tables 1 and 2. An example of using this optical system for the detection of carbon dioxide, hydrogen sulfide and pH are presented. In these model systems, the optical unit remains the same even though the indicator component changes.

Several model system examples will now be provided.

The optical system may comprise a yellow LED source and an output of 63 mcd at a peak wavelength of 590 nm. The detector is a silicon photodiode with a peak sensitivity at 720 nm and 0.37 W/A sensitivity at 660 nm.

A model system for the detection of $CO_2$ is disclosed below. The fluorescent material carboxnaphthofluorescein is suspended in a matrix of carbon dioxide-permeable silicone polymer. Included in this matrix is an aqueous emulsion of Bromthymol Blue indicator. The fluorescent material is excited by using the yellow LED with a peak emission of 590 nm and band width of 40 nm. This corresponds well to the peak absorbance for the fluorescent material carboxynaphthofluorescein at 598 nm. The emission of the fluorescent material is maximum at 660 nm. The sensor is an equilibrium with the carbon dioxide present in the media and this results in the aqueous emulsion of the sensor having a pH of greater than 7.6. If bacteria are present in the sample, the $CO_2$ produced thereby defuses through the silicone membrane into the aqueous emulsion and reduces the pH of the emulsion. As the pH is reduced, more of the Bromthymol Blue indicator is converted to the acid form and the color of the emulsion changes from blue to yellow (e.g., peak absorbance changes from 617 nm to 470 nm and the yellow light is not strongly filtered out).

When the indicator is in the base form (blue) it filters out the excitation light and no fluorescent signal is detected. As the pH and the emulsion decreases and more of the base form is converted to the yellow acid form, and more yellow light is allowed to reach the fluorescent material and an optical signal is detected. The light intensity is found to increase with an increase in $CO_2$ concentration. Experimentally, however, the operational amplifier inverts the signal and in FIG. 3 the voltage signal is decreased with an increase in carbon dioxide.

A model system for the detection of hydrogen sulfide is set forth below. This system acts as a probe, that is, it responds to the presence of $H_2S$ in an irreversible manner. For microorganism detection, the system has a constant high level of signal in the absence of $H_2S$. The detection of the presence of $H_2S$ will be indicative of a particular group of microorganisms.

The system comprises a fluorescent base material, carboxynaphthofluorescein, suspended in a hydrogen sulfide-permeable silicone polymer. Included in the silicone matrix is a dilute aqueous emulsion of lead acetate. The sensor is illuminated by the yellow LED. The resultant fluorescent signal is detected by the silicone photodiode. In use, the probe provides a constant signal unless there are microorganisms in the sample container that produce hydrogen sulfide. The hydrogen sulfide is soluble in the liquid media and will diffuse into the silicone membrane. Once inside, the hydrogen sulfide will diffuse into the aqueous emulsion containing the colorless lead acetate solution. The hydrogen sulfide reacts with the aqueous lead acetate to produce an insoluble lead sulfide.

The lead sulfide precipitate is black in color and strongly absorbs and scatters both the excitation and emission light. This results in a decrease in the fluorescent signal at the photodiode detector. The signal will be proportional to the amount of hydrogen sulfide produced until the available lead acetate is completely reacted.

A model sensor system for pH measurement uses the same Bromthymol Blue indicator as does the carbon dioxide sensor. However, instead of having the gas-permeable silicon membrane, this sensor has the indicator immobilized on a support and protected by a hydrogen ion-permeable membrane. As the pH of the media changes, the ratio of Bromthymol Blue indicator in the acid to base form changes in a manner proportional to the hydrogen ion concentration. This change in color provides a change in the fluorescent signal that is also proportional to the hydrogen ion concentration. This value can be used to determine the pH, as pH= −log (hydrogen ion concentration). The range of this sensor is limited to the range in color change of Bromthymol Blue, 6.2 to 7.6 pH. This range, however, covers the physiological pH range. Should an increase in the range be required, there are other sensor systems listed herein that cover the range of pH from 4.7 to 8.0.

TABLE I

| Indicators: | Color-Change | Direction of light-intensity with $CO_2$ increase |
|---|---|---|
| Blue LED (470 nm) | | |
| Fluorophores: | | |
| 1-Acetoxypyren 3,6,8-trisulfonic acid | | |
| DCM 4-dicyanomethylene2methyl6(p-dimethylaminostyrol) | | |

TABLE I-continued

| Indicators: | Color-Change | Direction of light-intensity with $CO_2$ increase |
|---|---|---|
| 4H-pyran | | |
| p-Nitrophenol | C-Y | increase |
| m-Dinitrobenzoyleneurea | C-Y | increase |
| Azolitmin | R-B | decrease |
| Bromxylenol Blue | Y-G-B | decrease |
| Green LED (560 nm) | | |
| Fluorophores: | | |
| 7-Aminoactinomycin D | | |
| Nile Red | | |
| Rhodamine B | | |
| 3,6-Dihydroxy xanthone | C-B | increase |
| Cleves Acid | C-G | increase |
| Propyl Red | R-Y | decrease |
| Neutral Red | R-Y | decrease |
| Bromcresol Purple | Y-G-P | increase |
| Alizarin | Y-R | increase |
| Yellow LED (590 nm) | | |
| Fluorophores: | | |
| Thionin | | |
| 3,3-Dimethyloxadicarbocyanine | | |
| Carboxynaphtho Fluorescein | | |
| Naphtho Fluorescein | | |
| Sulforhodamine 101 | | |
| Cleves Acid | C-G | increase |
| Orcinaurine | C-G | increase |
| p-Nitrophenol | C-Y | increase |
| 3,6-Dihydroxy xanthone | C-B | increase |
| Bromxylenol Blue | Y-G-B | increase |
| Bromthymol Blue | Y-B | increase |
| Red LED (645 nm) | | |
| Fluorophores: | | |
| 3,3-Diethylthiadicarbocyanine | | |
| Nile Blue | | |
| Cleves Acid | C-G | increase |
| Azolitmin | R-B | increase |
| Bromcresol Purple | Y-G-P | decrease |
| Alizarin | Y-R | decrease |
| Propyl Red | R-Y | increase |

TABLE II

FLUORESCENT DYES AND PIGMENTS

| Abbr. | Dye | Absorbance Max. nm | Fluorescent Max. nm |
|---|---|---|---|
| HPTS | 1-Hydroxypyren3,6,8,-trisulfonic acid | 460 | 515 |
| APTS | 1Acetoxypyren3,6,8-trisulfonic acid | 460 | 515 |
| RHO-123 | Rhodamine 123 | 505 | 534 |
| RHO-110 | Rhodamine 110 | 510 | 535 |
| EO | EOSIN | 518 | 550 |
| 7-AAD | 7-Aminoactinomycin D | 523 | 647 |
| SFRHO-G | Sulforhodamine G | 529 | |
| RHO-6G | Rhodamine 6G Perchlorate | 530 | 556 |
| RHO-6G | Rhodamine 6G Perchlorate | 530 | 590 |
| EVA | Evans Blue | 550 | 610 |
| NIRE | Nile Red Phenoxazon 9 | 551 | 636 |
| RHO-B | Rhodamine B | 552 | 580 |
| RHO-B | Rhodamine B | 554 | 627 |
| PYRO | Pyronin B | 555 | 599 |
| SFRHO-B | Sulforhodamine B | 556 | 575 |
| DODC | 3,3-Dimethyloxadicarbocyanine | 582 | 660 |
| SFRHO-101 | Sulforhodamine 101 | 586 | 607 |
| NAPH-FLU | Naphtho Fluorescein | 594 | 663 |
| CARB-FLU | Carboxynaphtho Fluorescein | 598 | 660 |
| TION | Thionin | 599 | 850 |
| NIBL | Nile Blue A Perchlorate | 628 | 690 |
| DTDC | 3,3-Diethylthiadicarbocyanine | 653 | 760 |
| DOTCI | Methyl-DOTCI* | 682 | 718 |
| IR | IR 144** | 750 | 848 |

*Methyl 3,3'Diethyloxatricarbocyanine iodide
**2-2-(3-Dihydro-1,1-dimethyl-3-(3-sulfopropyl)-2H-benz(e)indol-2-ylidene)ethylidene)-2-2(4-(ethoxycarbonyl)-1piperazinyl)-1-cyclopenten-1-yl)-1,1-dimethyl-3-(3-sulfopropyl)-1H-benz(e)-indolium Hydroxide inner salt, compound with N,N-Diethylethanamine (1,1).

TABLE III

| ABBR. | INDICATORS | ACID FORM | COLOR CHANGE | BASE FORM |
|---|---|---|---|---|
| PYR | Propyl Red | 4.7 | R–Y | 6.6 |
| NIPH | p-Nitrophenol | 4.7 | C–Y | 7.9 |
| ACOL | Azolitmin | 5.0 | R–B | 8.0 |
| BROMCRE | Bromcresol Purple | 5.2 | Y–G–P | 6.8 |
| CHLORO | Chlorophenol Red | 5.4 | Y–R | 6.8 |
| DX | 3,6-Dihydroxy xanthone | 5.4 | C–B | 7.6 |
| ALI | Alizarin | 5.6 | Y–R | 7.2 |
| BROXBL | Bromxylenol Blue | 5.7 | Y–G–B | 7.5 |
| DPD | 3,6-Dihydroxy phthalic dini | 5.8 | B–G | 8.2 |
| NITEU | m-Dinitro-benzoyleneurea | 6.0 | C–Y | 7.8 |
| BROMBL | Bromthymol Blue | 6.2 | Y–B | 7.6 |
| AU | Aurin (Aosolic acid) | 6.3 | Y–P | 6.9 |
| PHENRE | Phenol Red | 6.4 | Y–O–R | 8.0 |
| CLEV | Cleves Acid | 6.5 | C–G | 7.5 |
| ORC | Orcinaurine | 6.5 | C–G | 8.0 |
| RES | Resolic acid | 6.8 | Y–R | 8.0 |
| NEURE | Neutral Red | 6.8 | R–Y | 8.0 | pH-Indicators

B—blue —500 nm
G—green 510–590 nm
Y—yellow 590–620 nm
O—orange 620–640 nm
R—red 640–700 nm
P—purple 700–750 nm
C—colorless As indicated above, according to invention, optodes are provided for selecting detection of at least one substance from the group of $CO_2$, $O_2$, $A_22$, $A_2$, $H^+$ (pH), $Nh_4^+$ metal ions and $H_2S$, that are present during the metabolic process, as initial, intermediate or the final products.

The excitation and detection assembly may comprise a LED light source and a photodiode detector as well as a two-armed optical waveguide transmitting excitation radiation to the optode or optodes at carrying of the optical signal to the detector.

In a preferred variation of the invention, the optodes are combined to form a multilayer sensor.

In a simple structure of the invention, the optodes are attached to the inside of the wall of a transparent container and are connected to the evaluation unit via the excitation and detection assembly that may be placed flush against the outside of the wall of the container. The optodes, which may be mass-produced inexpensively, are attached directly or with an adhesive to the inner surface of the wall of the sample container, which is then filled with the culture medium, sealed and stored. After the addition of the specimen, for example, a blood sample, the container is thermostat-controlled for the time required for the growth of the culture, and is shaken if necessary, whereupon the concentration of the substance subject to chemical reaction by the metabolic processes is measured, for example, with a suitable optically-filtered photodiode in close proximity to the optode.

According to the invention, it is possible to place at least the optodes in the gas space of the at least partially transparent container above the culture medium mixed with the sample, and to use these optodes for measuring the concentration of at least one gaseous metabolite.

It is provided in accordance with the further variation of the invention that the optodes be located on a transparent stopper used for sealing the container.

The method will also permit, however, to place the optodes in a portion of the container covered by the culture medium mixed with the sample, possibly at the bottom of the container, and to use the optodes for measuring the concentration of at least one substance in the culture medium. With this arrangement, the metabolite is measured immediately at the place where it is produced, which will permit more rapid assessment as to whether a culture is positive or negative.

According to a particularly favorable structure of the invention, there is provided a device for temperature control of the sample, in which several containers are placed in labeled positions at the same time, each container being assigned an excitation and detection assembly transmitting excitation radiation through the optodes located in each container and detecting the ensuing optical signal, and the signals of the detection assembly are carried to an evaluation unit together with a position identification signal. The device used for temperature control may be configured as a temperature-controlled supporting rack with multiple optical stations, which will permit a large number of culture models, e.g., up to 600, to be monitored simultaneously. As compared to conventional equipment of this kind, no further handling of the samples is required once they have been filled into their individual bottles, since both the incubating process and the continuous monitoring are fully automated in the device of the present invention. Unlike conventional measuring techniques, in which the individual culture bottles must be inserted into an evaluation unit by hand once or twice daily, the technique of taking measurements continuously will allow the point in time when a culture becomes positive to be determined without delay. One or more substances involved in the metabolic process may be assessed optically and the presence of microorganisms may be determined very quickly. Therefore, a highly-sensitive automatic measuring system permitting noninvasive, continuous measuring techniques is provided by the invention. The evaluation unit either includes a microcomputer/microcontroller indicating the status of each individual container, or it is connected to a computer via an interface. Information useful for bacterial identification would be available with multiple optodes.

In another structure of the invention, provisions are made for a device for temperature control of the sample, which holds several containers at the same time, and for a feed mechanism or sample changer automatically taking the individual containers to a measuring station, in which the optodes located in each container enter into optical contact with the excitation and detection assembly. Whereas the variation described in the foregoing paragraph has no moveable parts at all, this structure has a conventional sample changer for automatically taking each sample to a measuring station. The advantage of this arrangement is that the electronic or electro-optical equipment need not be so elaborate.

According to the invention, it is also possible to fasten the optodes at the tip of the probe to be inserted into the container, which probe contains light waveguide elements from the excitation and detection assembly. The probe may be inserted through an opening sealed by a septum and introduced into the culture medium mixed with the sample or into the gas space thereabove.

A further variation of the invention provides that the container be sealed by a septum which may be punctured with a hollow needle of a sampling vessel, the optodes being located in the sampling vessel and a flow connection being established between the gas space of the container and the optodes via the hollow needle of the sampling vessel, after the sample has been added to the culture medium in the container. As a sampling vessel an evacuated vessel may be used, for example, to whose inner wall surface optodes may be affixed. The sample, e.g. blood, is sucked into the container by the vacuum applied to the vessel. The septum of the container holding the culture medium is pierced with the needle and the blood is introduced into the culture bottle. In view of the hollow needle, metabolic gases are conveyed from the gas space above the culture medium to the sensor, where they are measured. The culture bottle and sampling vessel are preferably designed as single-use articles that are discarded after use.

BRIEF DESCRIPTION OF THE DRAWINGS:

Other objects, features and advantages of the invention, its organization, construction and operation will be best understood from the following detailed description, taken in conjunction with the accompanying drawings, on which:

FIGS. 8, 9 and 10 are graphic illustrations of curves of measured concentrations; and FIG. 11 is a graphic illustration of measured curves using the sensor of the present invention to detect the growth of a variety of bacteria commonly found in cases of bacteremia.

DESCRIPTION OF THE PREFERRED EMBODIMENTS

Figure 1:
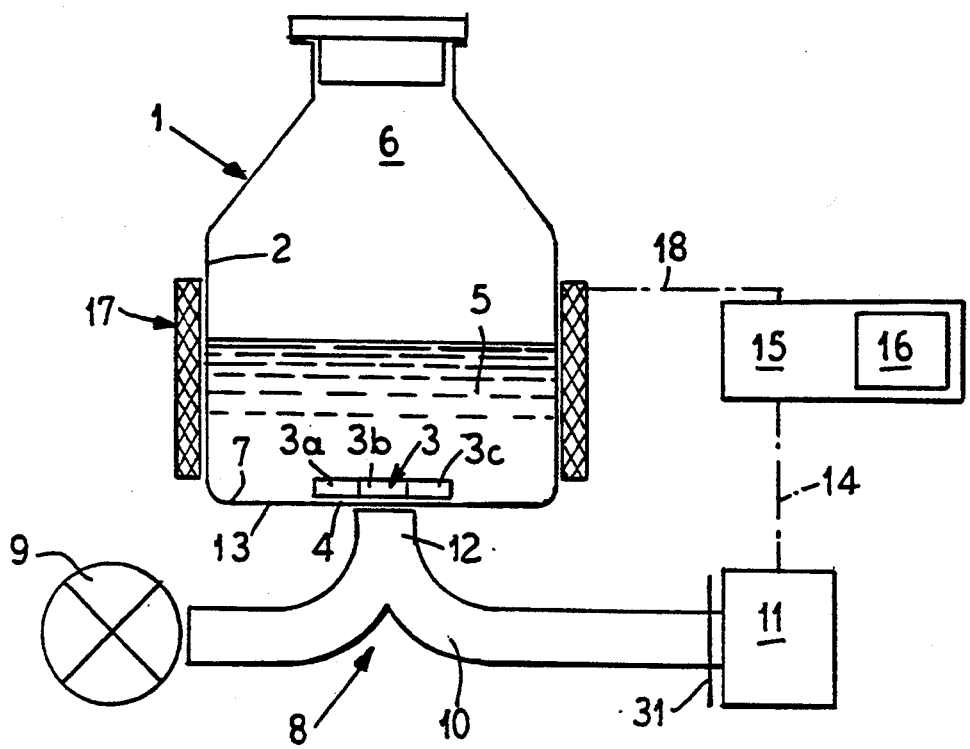
FIG. 1 is a schematic representation of a device for practicing the invention.

The device of FIG. 1 for detecting biological activities in a sample comprises a sealable, optically-transparent container 1 with an optode 3 attached to the inner surface 2 of its wall and bonded by a transparent adhesive layer 4.

Instead of a single optode 3 for a substance to be assessed, two or more optodes, 3a, 3b, and 3c may be combined into a multilayer sensor, which will permit simultaneous detection of the changes in $O_2$ and $CO_2$ concentrations and in pH, for example. The individual optodes 3a—3c or their indicator media may be stacked in layers one above the other, or they may be imbedded in a polymer membrane in homogenous distribution. The combination of a $C_2$ and an $O_2$ optode into a sensor is described in the European application O 105 870, for example.

Instead of the optode 3 in the variations discussed below, optodes may be provided for measuring $O_2$, $Co_2$, $H^+$ (pH), $Nh_4+$, $H_2S''$ and $H_2$, or rather, a specific combination of these optodes in accordance with the particular requirements.

The container 1 contains the culture medium 4 with one carbon compound (glucose), for example, which is converted by metabolic processes of microorganisms in the sample and to metabolic product, for example $CO_2$, during which processes $O_2$ is being consumed and the pH is subject to change. As a consequence, there are changes in the concentration of the metabolic product and the initial substances and the gas space 6 above the culture medium 5 and in the culture medium itself, which are detected by way of the optodes 3a, 3b, and 3c placed at the bottom 7 of the container 1 in FIG. 1. The excitation and detection assembly 8 comprises a light source 9, a detector 11 and a two-armed light waveguide 10, one of whose arms is coupled to the light source 9 and the other of which is coupled to the detector 11. The end 12 of the light waveguide is placed flush against the exterior 13 of the wall of the container, transmitting excitation radiation towards the optodes 3a, 3b and 3c through the transparent wall of the container, while receiving the optical signal, e.g., the fluorescence radiation emitted by the optodes.

The use of a suitable filter 31, for example, a filter disc, at front of the detector 11 will ensure that the signals are assigned to their corresponding optodes 3a, 3b, 3c.

By way of a line 14, the detector signals are transmitted to an evaluation unit 15 in which the change over time, e.g., of the $CO_2$ content is determined and the status of the sample is indicated via a display 16.

The conditions in the container necessary for the metabolic processes are maintained by way of the unit 17, which is mainly responsible for proper temperature control of the sample, and is connected with the evaluation unit 15 via a control lead 18.

Instead of a heating unit 17, an air heating element may be used for sample temperature control of the variation of FIG. 1 and all subsequent variations.

Figure 2A:
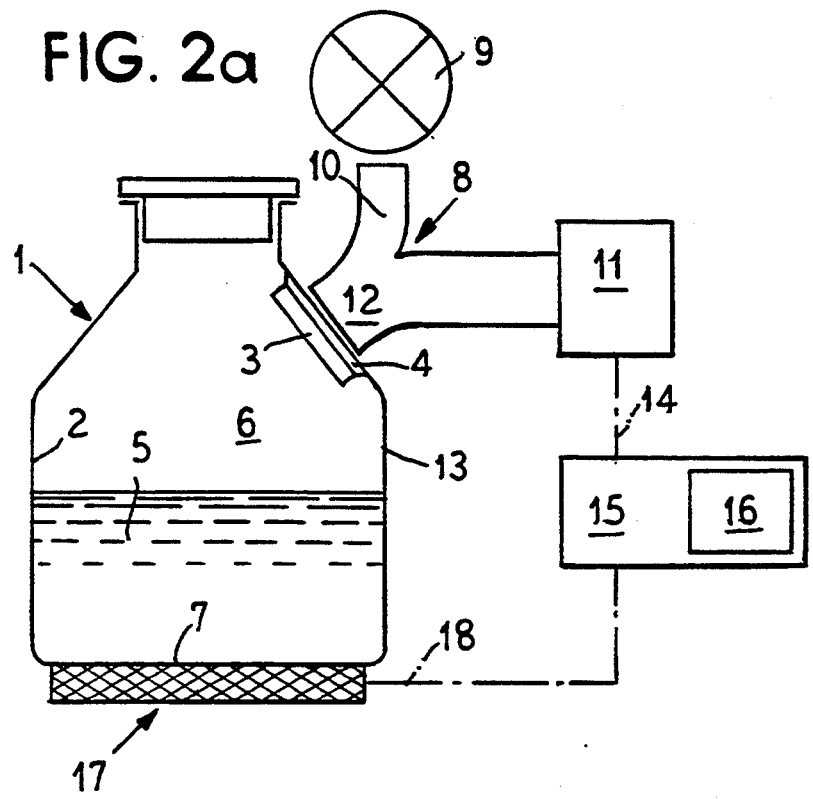
FIGS. 2a, 2b, 2c, 2d, 2e, 3, and 4 are similar views of variations of the device of FIG. 1.
Figure 2B:
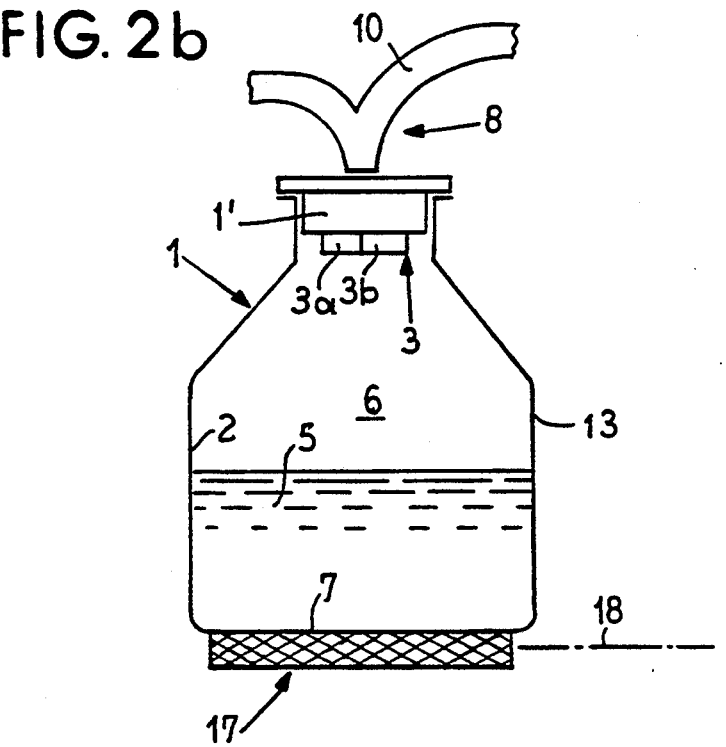
Figure 2C:
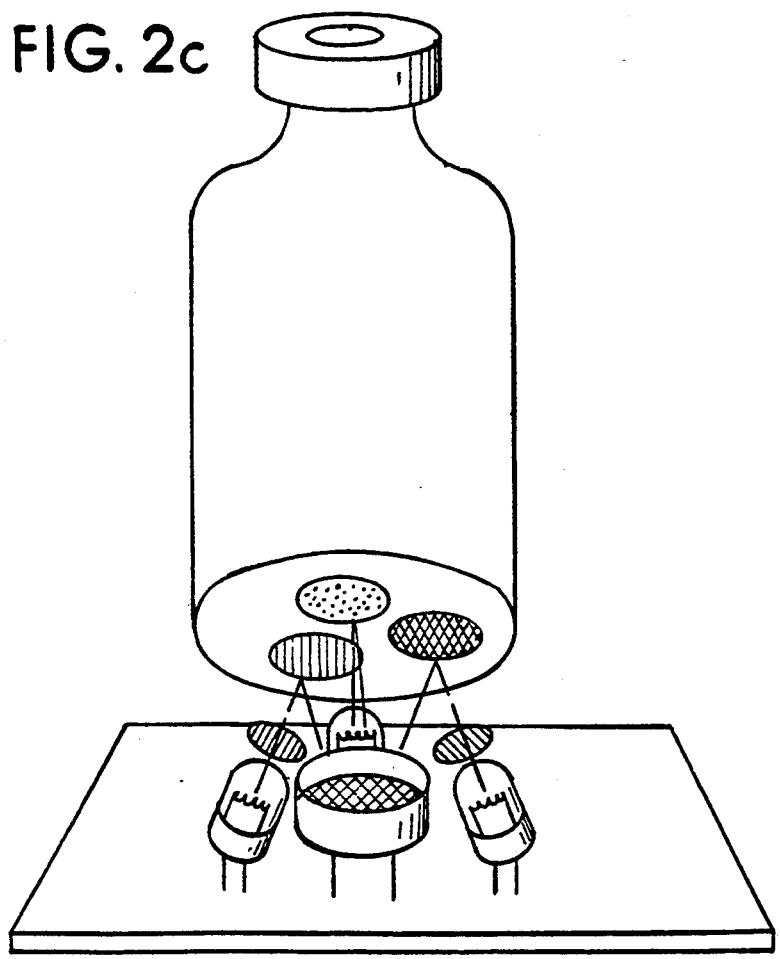
Figure 2D:
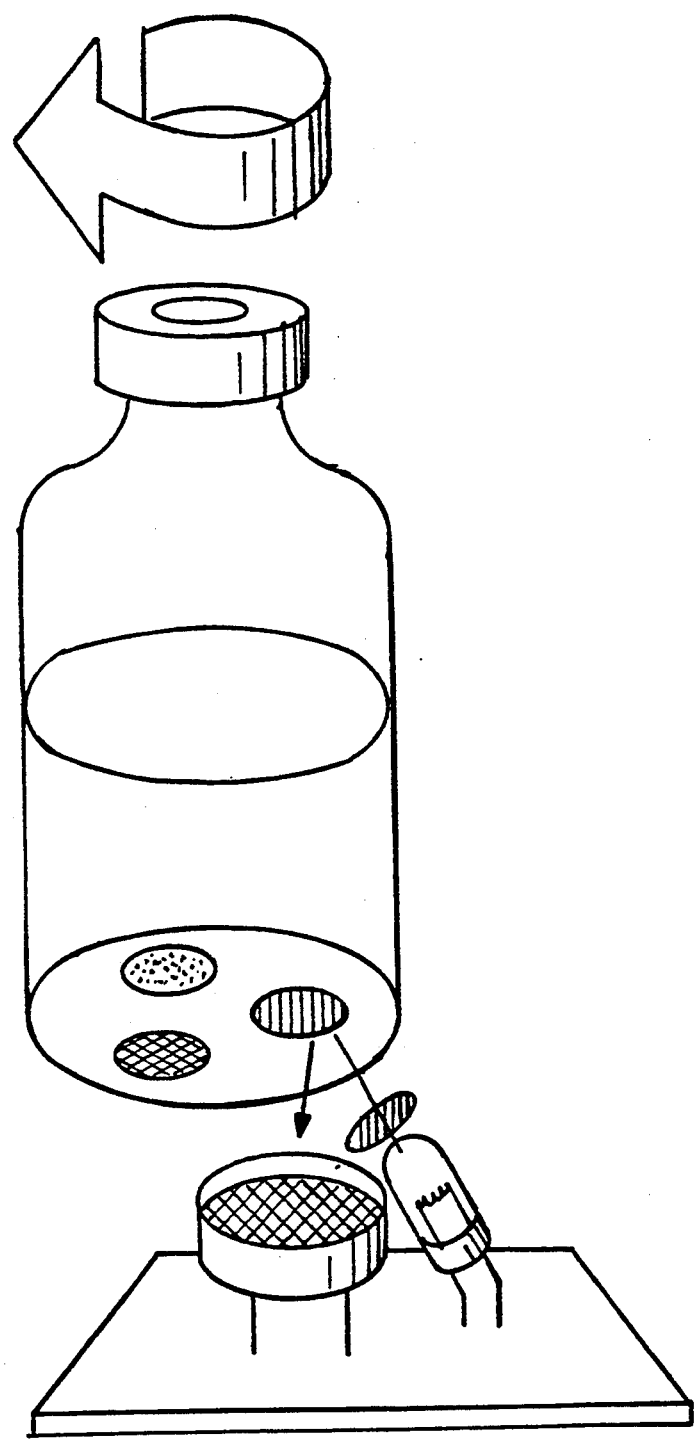
Figure 2E:
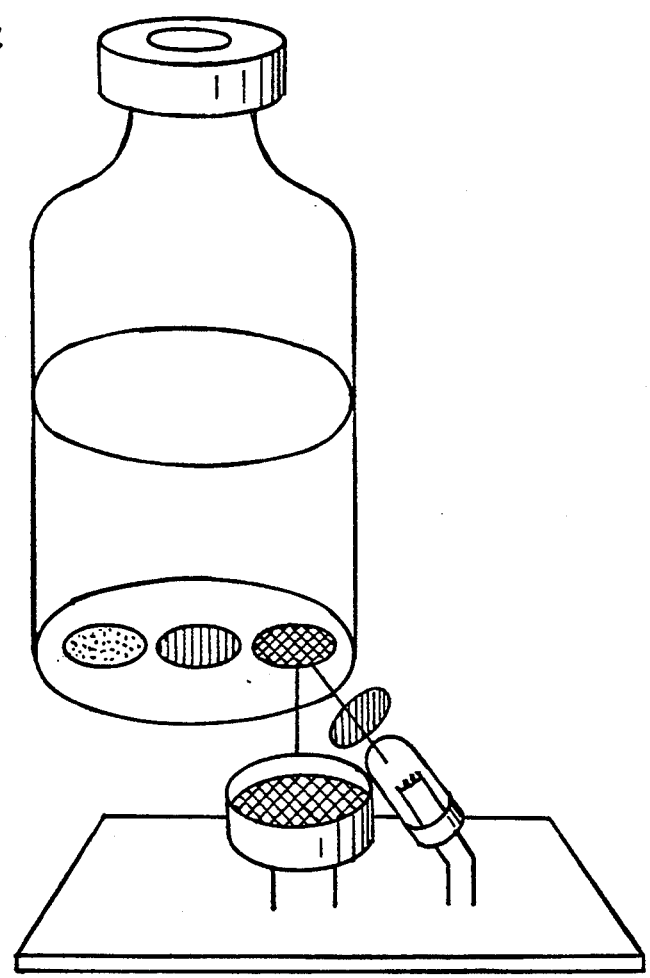

The structure illustrated in FIG. 2a differs from that of FIG. 1 only by the fact that the optode 3 is located in the gas space 6 of the container 1 and that the metabolites may be measured only. In this instance, temperature control is performed via the bottom 7 of the container 1. In a structure according to FIG. 2b, the optode 3, or the optodes 3a, 3b, may be attached to a stopper 1' sealing the container 1. The light waveguide 10 may go either through this stopper 1' or it may be placed on the exterior of the transparent stopper 1', as is shown in FIG. 2b. FIGS. 2c, 2d and 2e illustrate other modifications of FIG. 1 which utilize LEDs and photodiode detectors even though each optode has a different chemistry and produces a different optical change (e.g., color). The sensor's optical system is being used because the fluorescence is being measured.

Figure 3:
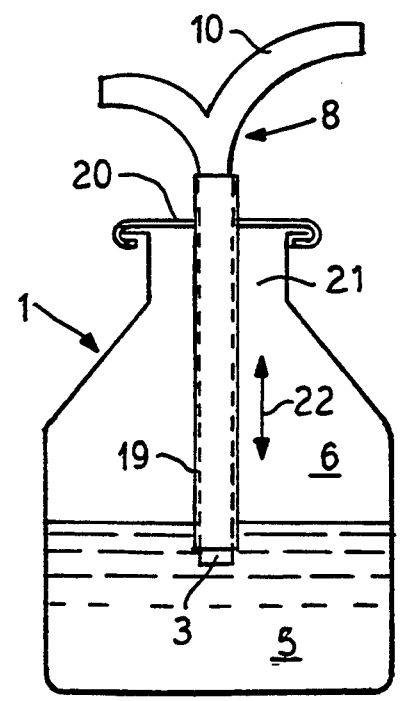

In another structure as presented in FIG. 3, the optode 3 is attached to the tip of a probe 19 receiving the end of the two-armed light waveguide 10. The probe 19 is introduced into the container 1 through the opening 21 sealed by a septum 20, and may be axially shifted along in the direction of the arrow 22, permitting measurements to be taken both in the gas space 6 and in the culture medium 5.

Figure 4:
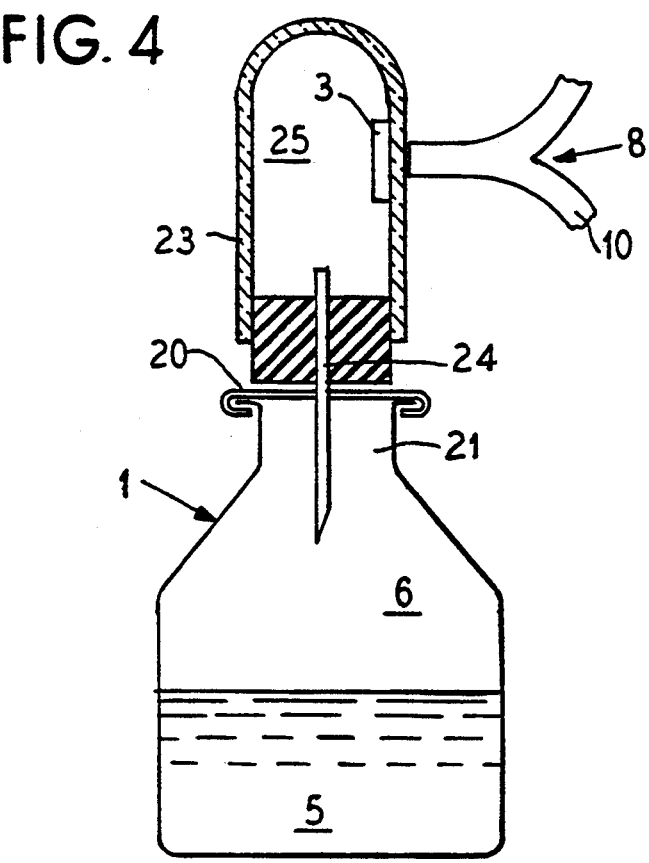

In the structure illustrated in FIG. 4, the optode 3, which is used, for example, for measuring $O_2$ and $CO_2$, is not located in the container 1, but is placed in a sampling vessel 23. In order to introduce the sample into the culture bottle, the septum 20 of the container 1 is punctured with the hollow needle 24 of the sampling vessel 23, permitting the sample to enter the culture medium. Via the hollow needle 24 a gas exchange will take place between the gas space 6 and the interior 25 of the sampling vessel 23 such that the change in the concentration of $CO_2$ and $O_2$ may be determined with the use of the excitation and detection assembly 8 which is symbolically indicated by the light waveguide 10.

Figure 5:
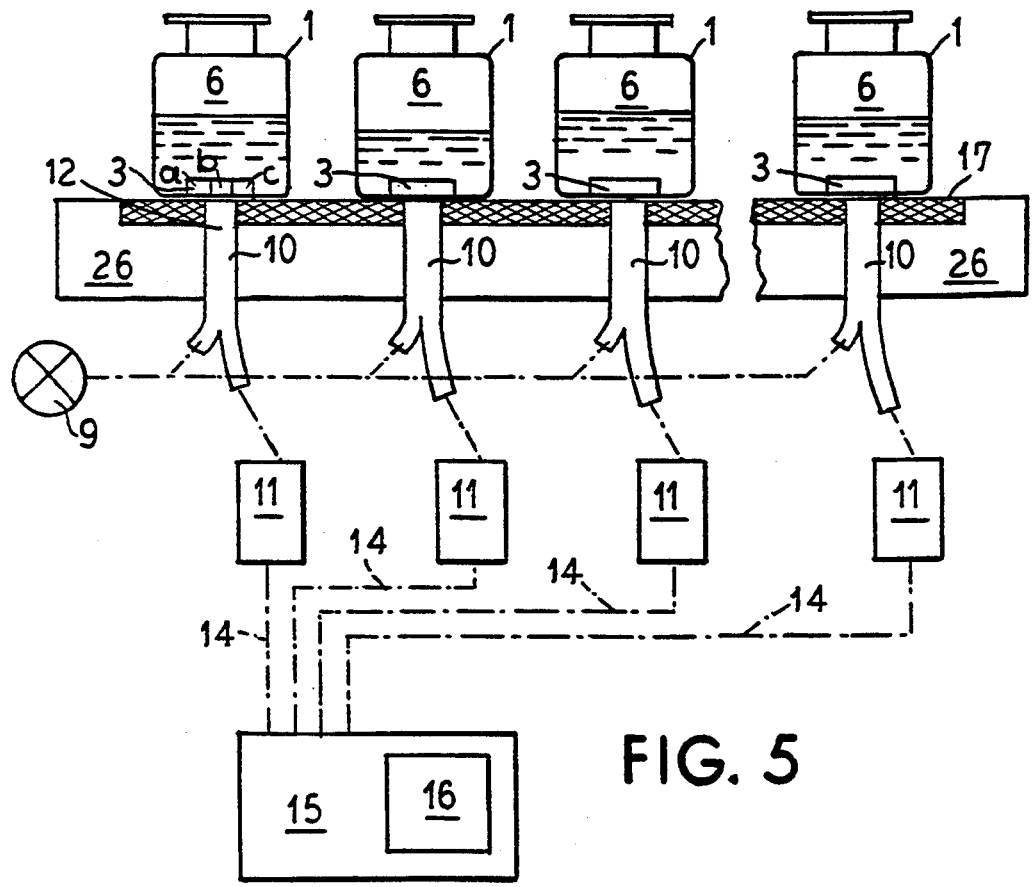
FIG. 5 is a schematic representation of a variation for automatic measuring of several containers at the same time.

A particularly favorable structure is illustrated in FIG. 5 comprising a device 26 configured as a temperature-controlled supporting rack, which will hold several containers 1 at the same time. The containers are inserted in labeled positions and are arranged in several rows, permitting temperature control and continuous monitoring of up to 600 containers simultaneously. Each container is assigned a two-armed light waveguide 10 located in the supporting rack 26 and providing the optodes 3a—3c at the bottom of each container 1 with excitation radiation. The corresponding optical signals are delivered to the individual detectors 11 connected to the evaluation unit 15 via lines 14. The individual readings delivered to the evaluation unit 15 are accompanied by suitable position identification signals such that the individual values may be directly assigned to the corresponding sample.

Figure 6:
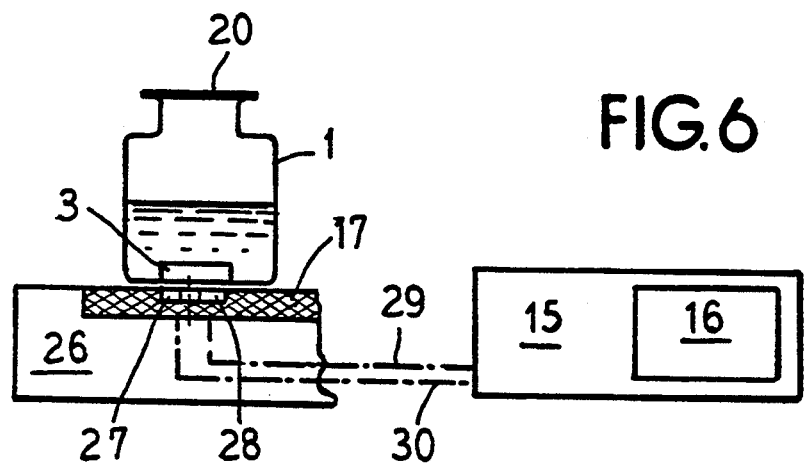
FIGS. 6 and 7 are schematic representations of variations of the structure of FIG. 5.

A structure as presented in FIG. 6 provides that each individual container 1 be connected with a LED 27 located in the supporting rack 20 and with a photodiode 28, possibly in conjunction with photo elements. In this manner, a most compact device is obtained which is characterized by the total absence of moveable parts.

Figure 7:
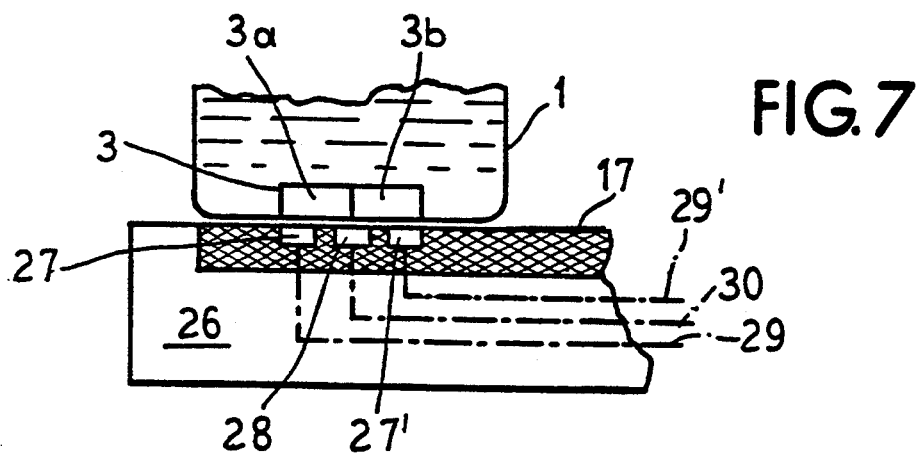

FIG. 7 illustrates a structure according to FIG. 6, which contains two optodes, 3a and 3b, combined into a sensor (e.g., a bisensor), for simultaneous measurement of $O_2$ concentration and pH. The optodes are excited via different LEDs 27 and 27' whose emission radiation is received by a common photodiode 28. The corresponding electrical leads 29, 29', 30 lead to the evaluation unit not shown here. By means of known optical or electronic equipment, the signals of the two optodes may be separated. Other variations with only one LED for excitation and several photodiodes for signal detection are within the scope of this invention.

In the graphic illustrations of FIGS. 8 and 9, the time t, or rather, the individual points in time $T_0$ to $T_8$ are plotted on the abscissa, while the pH value, the concentration K (or the partial pressure of $O_2$ and $CO_2$) and the number of bacteria or organisms per unit volume (logarithmic scale) are plotted on the ordinate.

FIG. 8 illustrates the change over time of the parameters $O_2$, $CO_2$ and pH using a sample containing Staphylococcus areus. Between the times $T_5$ and $T_6$ the concentration of $CO_2$ is characterized by a significant increase indicating a positive sample, and about the same time the $O_2$ and pH levels decrease.

As opposed to FIG. 8, the pH value in FIG. 9 remains largely unchanged, whereas the $O_2$ decrease occurs significantly sooner than the $CO_2$ increase. In this instance, a sample with Psaudomonas aeruginosa was used.

The values provided in FIG. 10 are taken from a sample containing enterobacteria (E. coli). All three parameters change and once again the $O_2$ decrease was noticed prior to the changing of the other parameters.

The method and device described herein are well-suited for detecting biological activities and samples, for example, of microorganisms in blood, (bacteriemia, septicemia or pyemia).

The continuous, noninvasive monitoring of specimens helps to obtain fully automated incubation and measuring processes for a large number of samples. Positive cultures are quickly identified and erroneous negative findings are avoided.

Although we have described our invention by reference to particular illustrative embodiments and examples thereof, many changes and modifications of the invention may become apparent to those skilled in the art without departing from the spirit and scope of the invention. We therefore intend to include within the patent warranted hereon all such changes and modifications as may reasonably and properly be included within the scope of our contribution to the art.

We claim:

1. A method for detecting biological activity in a specimen in a mixture with a culture medium capable of sustaining the growth of microorganisms exhibiting a metabolic activity which alters the concentration of at least one substance concentration in said mixture, said method comprising the steps of:
   disposing said mixture in a sealable, transparent container having an inner surface and an outer surface;
   exposing said mixture in said container to light from a light source disposed externally of said container;
   attaching a sensor to said inner surface of said container having a sensor surface exposed to said mixture and permeable by said substance, said sensor including an inert fluorophore responsive to light from said light source to emit fluorescent radiation of a predetermined wavelength;
   detecting said fluorescent radiation; and
   dispersing an indicator means in said container, between said fluorophore and said light source, which is optically responsive to a change in the concentration of said substance and thereby amplitude-modulating said fluorescent radiation of said predetermined wavelength to a degree corresponding to said change in said concentration of said substance.

2. A method as claimed in claim 1 wherein the step of dispersing an indicator means in said container is further defined by dispersing an indicator means in said container between said fluorophore and said light source for altering light from said light source, before said light reaches said inert fluorophore to amplitude-modulate said radiation emitted by said inert fluorophore.

3. A method as claimed in claim 1 wherein the step of dispersing an indicator means in said container is further defined by dispersing an indicator means in said container between said fluorophore and said light source for altering said fluorescent radiation emitted by said inert fluorophore, to amplitude-modulate said radiation emitted by said inert fluorophore.

4. A method as claimed in claim 1 comprising the additional steps of:
   selecting said inert fluorophore from the group consisting of Thionin, 3,3-Dimethyloxadicarbocyanine, Carboxynaptho Fluorescein, Naptho Fluorescein and Sulforhodamine 101; and
   selecting said indicator means from the group consisting of Cleves Acid, Orcinaurine, p-Nitrophenol, 3,6-Dihydroxy xanthone, Bromxylenol Blue and Bromthymol Blue.

5. A method as claimed in claim 1 comprising the additional steps of:
   containing said inert fluorophore in a $CO_2$-permeable silicone polymer matrix material of said sensor;
   selecting said inert fluorophore from the group consisting of 3,3-Diethylthiadicarbocyanine and Nile Blue; and
   selecting said indicator means from the group consisting of Cleves Acid, Azolitmin, Bromcresol Purple, Alizarin and Propyl Red.

6. A method as claimed in claim 1 comprising the additional steps of:
   selecting said inert fluorophore from the group of dyes and pigments consisting of 1-Hydroxypyren 3,6,8-trisulfonic acid, 1-Acetoxypyren 3,6,8-trisulfonic acid, Rhodamine 123, Rhodamine 110, EOSIN, 7-Aminoactinomycin D, Sulforhodamine G, Rhodamine 6 G Perchlorate (530 nm absorbance, 556 nm fluorescence), Rhodamine 6G Perchlorate (530 nm absorbance, 590 nm fluorescence), Nile Red Phenoxazon 9, Rhodamine B (552 nm absorbance, 580 nm fluorescence), Rhodamine B (554 nm absorbance, 627 nm fluorescence), Pyronin B, Sulforhodamine B, 3,3-Dimethyloxadicarbocyanine, Sulforhodamine 101, Naptho Fluorescein, Carboxynaptho Fluorescein, Thionin, Nile Blue A Perchlorate, 3,3-Diethylthiadicarbocyanine, methyl 3,3' diethyloxatricarbocyamine iodide and 2-2-(3-Dihydro-1,1-dimethyl-3-(3-sulfopropyl)-2H-benz(e) indol-2-ylidene)ethylidene)-2-2(4-(ethoxycarbonyl)-1piperanzinyl)-1-cyclopenten-1-yl)-1,1-dimethyl-3-(3-sulfopropyl)-1H-benz(e)-indolium Hydroxide inner salt, compound with N,N-Diethylethanamine (1,1); and selecting said indicator means from the group consisting of Propyl Red, p-Nitrophenol, Azolitmin, Bromcresol Purple, Chlorophenol Red, 3,6 Dihydroxy xanthone, Alizarin, Bromxylenol Blue, 3,6 Dihydroxy phthalic dini, m-Dintrobenzoyleneurea, Bromthymol Blue, Aurin, Phenol Red, Cleves Acid, Orcinaurine, Resolic acid, and Natural Red.

* * * * *